(12) United States Patent
Oginski et al.

(10) Patent No.: US 10,888,392 B2
(45) Date of Patent: Jan. 12, 2021

(54) BUSHING, SUPPORT ARM, AND SUPPORT SYSTEM FOR A MEDICAL TECHNICAL STAND APPARATUS

(71) Applicant: Ondal Medical Systems GmbH, Hünfeld (DE)

(72) Inventors: Stefan Oginski, Fulda (DE); Axel Bode, Wöllstadt (DE); Markus Höser, Tann (DE)

(73) Assignee: Ondal Medical Systems GmbH, Hünfeld (DE)

( * ) Notice: Subject to any disclaimer, the term of this patent is extended or adjusted under 35 U.S.C. 154(b) by 43 days.

(21) Appl. No.: 15/329,565

(22) PCT Filed: Jul. 9, 2015

(86) PCT No.: PCT/EP2015/001397
§ 371 (c)(1),
(2) Date: Jan. 26, 2017

(87) PCT Pub. No.: WO2016/015820
PCT Pub. Date: Feb. 4, 2016

(65) Prior Publication Data
US 2018/0206936 A1    Jul. 26, 2018

(30) Foreign Application Priority Data

Jul. 30, 2014   (EP) .................................... 14002657

(51) Int. Cl.
*A61G 12/00* (2006.01)
*A61B 90/50* (2016.01)
(Continued)

(52) U.S. Cl.
CPC ............ *A61B 90/50* (2016.02); *A61G 12/004* (2013.01); *F16M 11/2014* (2013.01);
(Continued)

(58) Field of Classification Search
CPC ............. A61B 90/20; A61B 2090/571; A61B 2090/00477; A61G 12/004; A61G 12/002;
(Continued)

(56) References Cited

U.S. PATENT DOCUMENTS 3,240,925 A * 3/1966 Paschke .................. F21V 21/14
362/253
4,564,165 A * 1/1986 Grant ...................... E04B 9/006
248/317

(Continued)

FOREIGN PATENT DOCUMENTS

| CN | 201253259 Y | 6/2009 |
| CN | 106121946 A | 1/2010 |

(Continued)

*Primary Examiner* — Nkeisha Smith
(74) *Attorney, Agent, or Firm* — Seed IP Law Group LLP (57) ABSTRACT

A stand apparatus, which can be built and assembled/disassembled in a modular manner, is shown and described. In particular embodiments, a bushing for a stand apparatus for arrangement in an operation theater, comprising a coupling part, by means of which the bushing can be mounted on a connecting component of the stand apparatus about a rotational axis and/or along the rotational axis in a height-adjustable manner—in particular, on a spindle—and a section on which the bushing can be connected to a support arm of the stand apparatus, wherein the section is a mounting section, by means of which the bushing can be mounted on the support arm in a reversible manner—in particular, by means of one or more fastening means. Further embodiments comprise a support arm for fastening to a bushing, as well as a support system, consisting of at least one such bushing and one such support arm.

18 Claims, 7 Drawing Sheets

(51) Int. Cl.
*F16M 11/20* (2006.01)
*F16M 11/24* (2006.01)
*F16M 13/02* (2006.01)
*A61B 17/00* (2006.01)
*A61B 90/57* (2016.01)

(52) U.S. Cl.
CPC .......... *F16M 11/24* (2013.01); *F16M 13/027* (2013.01); *A61B 2017/00477* (2013.01); *A61B 2090/571* (2016.02); *F16M 2200/06* (2013.01)

(58) Field of Classification Search
CPC .. A61G 13/107; F16M 11/2014; F16M 11/24; F16M 11/08; F16M 13/027; F16M 2200/06; F21S 8/06; E04B 9/006; F16B 21/165; F16B 21/16
USPC ............ 248/544, 317, 324, 343, 342, 282.1, 248/283.1, 289.11, 327
See application file for complete search history.

(56) References Cited

U.S. PATENT DOCUMENTS

| | | | | |
|---|---|---|---|---|
| 4,997,155 A * | 3/1991 | Reuter | ............... | F16M 11/08 248/278.1 |
| 5,460,894 A * | 10/1995 | Munch | ............... | F16M 13/02 174/68.3 |
| 6,030,103 A * | 2/2000 | Gampe | ............... | F21V 21/26 362/287 |
| 6,095,468 A * | 8/2000 | Chirico | ............. | F16M 11/2014 248/125.7 |
| 6,328,458 B1 * | 12/2001 | Bell | ............... | F16M 11/10 362/288 |
| 6,607,086 B1 * | 8/2003 | Gretz | ............... | E04B 9/006 211/123 |
| 6,779,767 B2 * | 8/2004 | Kuhn | ............... | F16M 11/08 248/276.1 |
| 6,817,585 B2 * | 11/2004 | Wagner | ............... | F16M 11/10 248/324 |
| 6,889,943 B2 * | 5/2005 | Dinh | ............... | B60N 2/073 248/343 |
| 7,097,145 B2 * | 8/2006 | Turner | ............... | F16M 11/10 248/274.1 |
| 7,516,924 B2 * | 4/2009 | White | ............... | A61B 90/50 248/123.11 |
| 8,091,849 B2 * | 1/2012 | Ayadhi | ............... | F16F 15/08 248/317 |
| 8,876,075 B2 * | 11/2014 | Diez | ............... | F16M 11/2014 248/274.1 |
| 9,022,339 B2 * | 5/2015 | Borg | ............... | H02G 3/0493 248/323 |
| 9,038,969 B2 * | 5/2015 | Neuhof | ............... | F16M 11/04 248/74.1 |
| 9,458,952 B2 * | 10/2016 | Zhang | ............... | F16M 13/027 |
| 9,532,843 B2 * | 1/2017 | Palmerton | ............. | B01D 53/04 |
| 10,080,696 B2 * | 9/2018 | Oginski | ............... | A61G 13/107 |
| 2003/0132356 A1 * | 7/2003 | Copeland | ............ | F16M 11/041 248/282.1 |
| 2004/0262474 A1 * | 12/2004 | Boks | ............... | F16M 11/041 248/276.1 |
| 2008/0086150 A1 | 4/2008 | Mathis et al. | | |
| 2018/0140377 A1 * | 5/2018 | Reichenbach | ........ | A61B 90/50 |
| 2018/0259122 A1 * | 9/2018 | Reavill | ............... | A61B 90/35 |

FOREIGN PATENT DOCUMENTS

| | | |
|---|---|---|
| CN | 101889900 A | 11/2010 |
| CN | 202143653 U | 2/2012 |
| CN | 202605025 U | 12/2012 |
| CN | 103536364 A | 1/2014 |
| DE | 10 2004 054 866 B3 | 8/2006 |
| DE | 10 2012 112 712 A1 | 6/2014 |
| WO | 2010/072212 A1 | 7/2010 |

* cited by examiner

BUSHING, SUPPORT ARM, AND SUPPORT SYSTEM FOR A MEDICAL TECHNICAL STAND APPARATUS

BACKGROUND

Technical Field

The present disclosure relates to a bushing for a stand apparatus for arrangement in an operating theater, which bushing is set up to mount a support arm or a medical technology device on a spindle. The present disclosure also relates to a support arm that can be fastened to the bushing. The present disclosure also relates to a support system having at least one such bushing and having at least one such support arm. The present disclosure relates in particular to a bushing having individual features of claim 1, as well as a support arm and a support system respectively having individual features of the corresponding independent device claim.

Description of the Related Art

Stands—in particular, ceiling stands, e.g., ceiling supply units, monitor supports, or what are known as spring arms or central axles—most often have multiple support arms arranged rigidly relative to a vertical position or so as to be height-adjustable, by means of which support arms a medical technology device that is fastened thereto may be moved and positioned, e.g., in an operating theater—in particular, also in an intensive care unit. Supply units are often mounted on the stands, at which supply units are arranged, for example, medical-electrical bedside terminals that, for example, are supplied with the required media during an operation. The supports/support arms thereby define an action radius of the medical technology device in which said medical technology device may be positioned within the operating theater. The support arms may therefore also be designated as booms. The support arms may for the most part be rotated around at least one rotatable connection—in particular, a swivel joint. Alternatively, the support arms are also height-adjustable and/or are arranged so as to be pivotable in their height around an at least approximately horizontally aligned axis.

An optimally simple type of mounting and a high degree of stability are desirable with such stands. The individual support arms of the stand thereby form a support system which often comprises multiple joints or bearings—in particular, pivot joints. A respective support arm then must be connected with these joints or bearings. As is known, this may be ensured via a welded connection between a support arm and, for example, a bushing, particularly if the components are made from structural steel. However, a weld or a welded connection often has the disadvantage that material stresses and possibly also distortion are caused in the support system. In particular, in more complex support systems, this may lead to the situation where individual components can no longer be aligned exactly relative to one another, or the joints/bearings are not symmetrically loaded. The support system then possibly pivots—due to the action of gravitational forces—independently and unpredictably in a certain direction, and therefore would not be usable without a locking brake. It may even occur that the individual components cannot at first be assembled/coupled with one another at all during assembly. This leads to a costly, time-consuming assembly, to necessary correction measures, or to rejection and increased consumption. In order to remedy this problem, the bearing surfaces in the joints might, for example, be incorporated or reworked only after the production of the welded connection; this is, however, very costly.

A welded connection may also be disadvantageous, for the following reasons. Specific materials that can be welded well must be used. The material selection is limited. In particular, structural steel is normally preferred—not least because of cost. Structural steel has a high weight. A welded support system accordingly most often also has a high intrinsic weight, which also hinders the assembly and requires correspondingly dimensioned, costly joints, especially with more complex stand systems. The complete system is then very inert and cannot be repositioned without considerable manual or motorized expenditure of force. This may have great disadvantages in an operation, particularly if the operation must take place over a long time period of multiple hours or days. Structural steel must additionally also be protected against corrosion, and thus in many instances requires a coating—in particular, a powder coating. However, corrosion damage cannot be avoided even with a coating—particularly not in cavities or grooves for cables.

In many instances, a welding or a welded connection additionally requires a high logistical (internal operation) cost, since, for example, the steps that are for the most part implemented in different spatial regions of an operation—pre-manufacturing, welding, post-processing, quality control of the weld seams, surface treatment, and final assembly—must be matched to one another. Not least, with automated welding, the risk exists that a welding robot is not set up exactly, such that a weld seam is incorrectly positioned and/or does not have the required depth. These errors are not simple to detect in a visual inspection.

BRIEF SUMMARY

It is an object of the present disclosure to provide an apparatus or arrangement for a stand—in particular, a ceiling stand—by means of which a stand may be designed, manufactured, and/or assembled in a simple manner, or by means of which the alignment or bearing adjustment, in particular, of the stand may be facilitated. In particular, the object consists in providing at least one component of a support system by means of which a modular design of the stand may be produced in a simple manner, especially also with regard to a particularly exact alignment. The object may also be seen as so designing a stand that it may be adapted in a simple manner to specific positions or arrangements in the operating theater.

This object is achieved via a bushing for a stand apparatus for arrangement in the operating theater, comprising a coupling part by means of which the bushing can be mounted on a connecting component of the stand apparatus about a rotational axis and/or along the rotational axis so as to be height-adjustable—in particular, on a spindle—and a section on which the bushing can be connected to a support arm of the stand apparatus, wherein the section is a mounting section by means of which the bushing can be mounted on the support arm in a reversible manner—in particular, by means of one or more fastening means. Multiple advantages can in this way be achieved. On the one hand, selection of materials can be largely free. On the other hand, a support system of modular design is provided. A readjustment may also take place in a simple manner. Different variants of booms or support arms may also be connected with one another. For example, an already mounted support arm may be exchanged for another, longer or shorter support arm, or for a support arm with a greater carrying capacity. A stand apparatus with such a bushing may, for example, be adapted simply, given a restructuring or functional conversion of the operating theater. Not least, the assembly may take place at freely selectable sections of the value chain.

The respective system component is not thermally stressed. No risk exists of a distortion or of material stresses in the respective system component. The assembly may take place in a simpler or more precise manner. A slant due to distortion may be avoided. A support system may be provided with which a medical technology device may be mounted in a predefined position in an exact alignment, without the support system necessarily needing to be anchored in the position by means of a locking brake.

Thanks to the type of reversible connection/coupling according to the disclosure, selection of the material of the respective system components may take place independently of the "weldable" requirement. For example, aluminum may be used without any problems. Not least, the bushing may therefore also be fastened/mounted reversibly to, for example, an extruded support arm profile. Weight-optimized—in particular, non-metallic—materials may also be selected. A coating or other corrosion protection is not necessary. For example, glass fiber- or carbon fiber-reinforced plastic (GRP or CRP) may be used.

It may in this way also be made possible to connect individual system components modularly with one another in different arrangements, such that a (respective) rotation axis can be arranged in a specific absolute spatial position. In particular, the spacing of individual rotation axes relative to one another in the horizontal direction may be varied, e.g., over the length of the support arm or a plurality of assembled support arms—in particular, support arms bolted to one another.

What is thereby preferably to be understood as "reversibly mountable" is an arrangement in which the components may be affixed to one another, and also may be disassembled again or be mounted on one another in a different position.

What is thereby to be understood as a stand apparatus is a device for retention, stationary arrangement, and/or repositioning of at least one medical technology device that may be firmly mounted or positioned on a wall (in a wall mount) or a room ceiling, or also in a floor of an operating theater or any other room for medical purposes—thus, a ceiling stand, for example. The stand apparatus is then not completely freely repositionable in the operating theater, but, rather, may be repositioned in a defined action radius—in particular, relative to a fastening point or mount point arranged on a room ceiling or wall of the operating theater. The stand apparatus may be designed as a ceiling supply unit installed at a room ceiling, and may have one or more supply consoles which are mounted and can be positioned on one or two support arms. The stand apparatus may also be designed as a monitor support. The stand apparatus may also be designed as what is known as a spring arm—in particular, a spring arm mounted on a wall—and have a lamp, for example. The stand apparatus may also be designed as what is known as a central axis—in particular, a central axis installed on a room ceiling—and have a plurality of support systems with respectively at least one support on which a monitor or a lamp is mounted, for example. The stand apparatus preferably has at least two support arms on which respectively at least one brake of the brake device may be provided. For example, locking brakes may be provided which brake firmly and only so lightly that a support arm is prevented from independently altering the position (drifting, swinging away). Such a locking brake may also be tightened down for assembly purposes.

What is thereby preferably to be understood as a medical technology device is a supply console by means of which means for treatment of a patient and/or instruments for a surgeon and/or light, clean air, or other media required in the operating theater may be provided. The medical technology device preferably has some sort of control panel and/or some sort of display device for graphically presenting patient data, for example.

What is thereby preferably to be understood as a coupling part is a part of the bushing by means of which the support arm or boom can be mounted on a spindle or other connection component that is arranged to be stationary—in particular, so as to be rotatable or height-adjustable. For example, the coupling part may form at least one part of a pivot bearing, e.g., annular bearing surfaces.

What is thereby to be understood as a connection component is preferably a component by means of which individual supports/support arms of the stand apparatus may be mounted so as to be rotatable and/or height-adjustable at a stationary anchor point—in particular, at a mounting device, e.g., a ceiling tube below a ceiling. With a stand apparatus in the form of what is known as a central axis, the connection component may be designed as a centrally arranged—in particular, rotationally symmetrical—spindle on which multiple supports or support arms are mounted.

According to one exemplary embodiment, the mounting segment is set up to fasten the bushing on the support arm in a positive and/or non-positive fit (preferably, at least essentially non-positive), without material bond, so as to be reversibly mountable/de-mountable at a predefined relative position. It may in this way be precluded that position inaccuracies occur during the assembly, or that the complete system (the stand apparatus) is not exactly aligned. For example, the fastening may take place by means of a screw connection that acts essentially non-positively.

According to one exemplary embodiment, the mounting segment has at least one lead-through for arrangement of a fastening means. The assembly may in this way be simplified, and a force transfer may take place at predefined attachment points. Preferably, the lead-through extends in a radial direction—in particular, at least orthogonal to the rotation axis. The fastening means may in this way mainly be subjected to tensile stress, or may also be assembled with a comparatively small pre-tension. The mounting segment preferably has at least two lead-throughs arranged preferably at a maximum distance from one another. Torques may in this way be effectively transferred.

The lead-through may be formed as a bore or countersink, for example. Multiple lead-throughs—in particular, four or more lead-throughs—are preferably arranged circumferentially along a contour corresponding to an outer contour of the support arm. Large supporting forces or moments may in this way be transferred.

According to one exemplary embodiment, the mounting segment has at least one placement surface facing toward the rotation axis, on which placement surface a fastening means can be placed for the transfer of a normal force that acts radially outward in a radial direction, essentially orthogonal to the rotation axis. An interface acting solely or at least essentially via non-positive fit may in this way also be provided between the bushing and the support arm.

According to one exemplary embodiment, the mounting segment is set up to fasten the bushing to the support arm in an essentially non-positive fit, via static friction, and/or by means of positive fit brought about non-positively. An interface may in this way be provided—in particular, a flat surface which may be produced simply and cost-effectively. A normal force producing static friction may thereby be transferred between the bushing and the support arm via, for example, fastening means in the form of bolts. Optionally, positive fit may also take place—for example, by means of any sort of shoulders, borders, or edges on the mounting segment. Non-positive fit preferably occurs in conjunction with positive fit. Via shoulders, locking means, or undercuts, the mounting segment may also provide a connection, given which a force must initially be applied in order to provide a positive-fitting coupling. Positive fit may thereby facilitate the assembly, or also increase the security or robustness of the coupling.

According to one exemplary embodiment, the mounting segment has a face directed radially outward, which face is designed to geometrically correspond to a face of the support arm, and, in particular, is arranged at least approximately in one plane. The assembly may in this way take place simply on a side at which forces and moments may be transferred effectively and via a comparatively large surface. The face preferably has a flat face surface which forms an interface with a geometrically correspondingly designed face surface (a mounting interface) of the support arm. This enables a flush arrangement, wherein the components may simply be produced with high precision of fit. Only high measurement tolerances, or no measurement tolerances at all, need to be observed. However, it has been shown that it is advantageous to design the components abutting one another with regard to specific perpendicularity tolerances—especially in order to ensure a particularly exact alignment of the support arms.

The mounting segment is preferably formed by at least one surface segment of the face that is aligned at least approximately parallel to the rotation axis. A simple design, a simple assembly, and/or a symmetrical introduction of force may in this way be ensured. According to a preferred variant, the face is formed by a flat face surface. This enables a simple post-processing of the mounting segment. An alignment of the stand may thereby also be readjusted in a simple or particularly exact manner.

According to an advantageous variant, the surface segment of the face is inclined slightly (approximately 0.2° to 0.5°, and particularly, 0.3°), such that—in the unloaded state—a support arm is aligned upwards and does not bend downwards or sag under load (gravitational force). In other words, the surface segment enables an alignment of the support arm in a very exact manner. The surface segment may thereby be post-processed in a comparatively simple manner.

The surface segment of the face is preferably of maximum size with regard to the cross section of the bushing in a plane parallel to the rotation axis ("radial cross section")—in particular, with regard to a good stability and/or in order to be able to transmit large bending moments. In the direction of the rotation axis, the radial cross section also preferably has at a minimum at least approximately the same (axial) length as the coupling part—in particular, for reasons of stability. According to one variant, the radial cross section may also be greater than the axial length of the coupling part, especially if this can ensure improved stability.

According to one exemplary embodiment, the mounting segment has a safety device to hold up the support arm—in particular, a safety device set up to hold the support arm independently of additional fastening means. This safety device not least facilitates the assembly—in particular, in that the support arm is mounted at/on the safety device until the support arm is completely fastened. The safety device may ensure a high safety factor and—in addition to fastening means—may act in the manner of a redundant safety device.

According to one exemplary embodiment, the safety device projects in the radial direction, wherein the safety device preferably has a cross section profile which is designed to geometrically correspond to the cross-section profile of the support arm. The cross-section profile of the safety device is preferably smaller than the cross-section profile of the support arm, such that the safety device may engage in the cross-section profile of the support arm. The safety device may thereby be designed in the manner of a plug-socket connection, wherein the support arm forms the side of the socket in which the safety device engages. The safety device is preferably designed as a longitudinal profile segment that projects radially from the bushing.

The support arm advantageously has an interior for rotationally fixed accommodation of the safety device (designed as a longitudinal profile) of the bushing, wherein, at one side of the interior, a bearing segment is formed that has a bearing surface facing the interior, the contour of which bearing surface corresponds with a support contour of the safety device of the bushing, such that, in the inserted state of the safety device in the interior, the bearing surface on the support arm is in—in particular, positive-fitting—contact with the corresponding support contour of the safety device at the bushing.

To mount the support arm at the bushing, the safety device can thus be inserted into the axially extended interior of the support arm. The support contour of the safety device or of the longitudinal profile segment thereby comes to rest on a corresponding bearing surface at the bearing segment of the support arm.

According to an exemplary embodiment, the safety device has a preferably concave support segment curved inward and downward, which support segment is set up to bear the support arm and support it in the vertical direction, wherein the support segment preferably extends at least approximately in the radial direction, orthogonal to the rotation axis. The support segment preferably has a contour which corresponds to a corresponding (in particular, convexly) curved inner contour of the support arm.

According to one exemplary embodiment, the mounting segment has at least one positive-fitting safety segment to counter vertical movement and/or twisting, or to counter axial movement and/or twisting. This improves the loading capacity of the mounting segment and may facilitate the assembly.

According to one exemplary embodiment, the mounting segment has a recess for conduits or cables—in particular, in the radial direction. This enables a repositioning of cables or conduits, independently of in what state of assembly the system is in. The recess for cables or conduits is preferably arranged above the safety device.

According to one exemplary embodiment, the bushing is in the shape of a fork and has at least two annular segments which form the coupling part—in particular, two annular segments with bearing seats for a pivot bearing. A stable, robust design may in this way be provided which requires less material usage and can transfer forces and moments at effective points.

According to one exemplary embodiment, the bushing is a cast part—in particular, of aluminum or an aluminum alloy. The bushing may in this way be functionally optimized and designed so as to save on materials. With a cast part, openings or shapes that may serve for the fastening of additional components can be additionally, cost-effectively cast as well. For example, if the bushing were to be produced as a welded construction made up of multiple plates, additional add-on parts would need to be fastened for the accommodation of, for example, brake screws, rotation angle stops, eyes for bolting on the casing, etc.

With aluminum (or an aluminum alloy) as a material for the bushing, rework that might possibly be required on the cast bushing can also be reduced or be executed in a simpler manner (lower material or power usage).

The aforementioned object is also achieved by a support arm for a stand apparatus for arrangement in an operating theater, having at least one interface at which the support arm can be connected with a bushing of the stand apparatus, wherein the interface is a mounting interface by means of which the support arm can be reversibly mounted at the bushing. The advantages cited previously in conjunction with the bushing in this way result, at least in part. The support arm may thereby be reversibly mounted in a positive and/or non-positive fit in a predefined relative position, without material bond. At least one receptacle for fastening of the bushing—in particular, by means of a fastening means, may be arranged at the mounting interface. The at least one receptacle is preferably arranged in a radially outward lying segment of a cross section profile of the support arm. This enables a stable connection or the transfer of large forces.

The support arm preferably has at opposite ends two at least approximately identically designed mounting interfaces. The support arm may in this way be mounted independently of its alignment. Multiple support arms may also be mounted on one another in a simple manner—in particular, without an adapter being necessary.

According to one variant, the forward and rear ends of the support arm are designed differently than one another, in that a positive-fitting safety device at the forward end of the medical technology device is dispensed with. It has been shown that—due to the lever arm—the load exerted on the forward mounting segment of the support arm is markedly less, such that a safety device may be omitted.

The cross-section profile of the support arm is preferably open to one side—in particular, above or below. This enables a repositioning of a cable via a lateral insertion of the cable. With a non-material bonding for the bushing, such a cable channel may thereby also be provided up to the bushing and be used. By contrast, this may not be possible with a welded joint, particularly if a weld seam must be provided around the circumference for reasons of strength.

The support arm preferably has a rectangular cross section profile, open to at least one side, with a top-side or underside cable channel. In the assembled state of the support arm, the cable channel is preferably open upward or downward, wherein the support arm may be surrounded by a casing, behind which a cable may be placed. The support arm is preferably formed by an extruded profile.

The support arm is preferably formed from aluminum or an aluminum alloy. The support arm is preferably formed from an extruded profile. The support arm preferably has rough-pressed recesses (in particular, screw channels) which are designed to geometrically correspond to the fastening means. This kind of receptacle also allows pressing tools to be produced in an especially stable manner, such that work may proceed at greater press speeds. The corresponding pressing tools may also be implemented cost-effectively. The receptacles preferably have inner threads.

The support arm preferably has a bearing segment which is set up to be borne at/on a safety device (in particular, on a support segment) of the bushing. The bearing segment is preferably convexly curved inward and downward, and is provided at the top side of the support arm. The bearing segment preferably has a bearing surface facing inward. According to one variant, the bearing segment thereby also simultaneously forms a cavity to accommodate cables—in particular, a cable channel accessible from above. This embodiment provides, on the one hand, high stability, and, on the other hand, good accessibility.

The bearing segment is set up to bear the support arm and hold it up in the vertical direction, wherein the bearing segment preferably extends at least approximately in the longitudinal direction of the support arm. The support arm may in this way be plugged onto the bushing in the radial direction. The cross-section profile of the support arm is preferably formed by a circumferential wall, wherein the at least one receptacle is preferably respectively formed in one corner of the wall. An inner surface of the wall may thereby form the receptacle. For example, an inner threading may be formed on the inner surface of the wall. The circumferential wall is preferably concavely curved inward to one side of the support arm—in particular, at the top side—such that a U-profile results in cross section. This U-profile may form a dimensionally stable bearing segment.

The aforementioned object is also achieved via a support system for a stand apparatus for arrangement in an operating theater, comprising at least one bushing according to the disclosure and at least one support system according to the disclosure, which support arm is mounted or can be mounted reversibly at the mounting segment of the bushing. The support system thereby comprises at least two components that can be reversibly mounted on one another in a predefined position relative to one another. Two bushings and a support arm preferably form a respective boom comprised of at least three reversibly mountable components, which boom is preferably mounted on a pivot bearing.

In the support system, the individual components may respectively be formed as cast parts or extruded profiles, for example. The material selection may take place independently of the other components.

According to one exemplary embodiment, the support system comprises fastening means, preferably in the form of screws, which are assembled or can be assembled at the mounting interface between the bushing and the support arm. The assembly may, for example, take place with a predetermined torqueing of the bolts, which may increase the safety and may make the connection durable. With fastening means in the form of bolts, for example, it may be documented in a simple way with what pre-tension the components are coupled to one another—in particular, with what torque the fastening means have been fastened. The fastening means may be assembled directly in the course of the final assembly, such that the entire production or assembly process is lean/efficient, and time and costs may be saved. The support arm is thus to be affixed to the bushing via at least one (preferably four) fastening means that, for example, are designed as bolts, which fastening means flank the safety device at one corner (preferably four corners), so that a connection between the support arm and the bushing is achieved that is both rotationally fixed and tight in the axial direction of the support arm or, respectively, in the radial direction of the bushing.

According to one variant, fastening means are provided in the manner of a plug connector element—in particular, over a greater length. For example, the plug connector element may be secured by additional laterally introduced pins, if desired.

The fastening means may be mounted or mountable in the radial direction, at least approximately orthogonally to the rotation axis, such that they can essentially be put under tension. This arrangement yields advantages with regard to distribution of force—in particular, also in connection with a mounting surface that is essentially flat and aligned parallel to the rotation axis. The fastening means preferably engages in a positive fit in the support arm. This enables a simple design and a simple assembly. For example, the fastening means must merely be plugged through lead-throughs/bores introduced into the bushing.

According to one exemplary embodiment, the support system comprises an additional bushing which is mounted or can be mounted reversibly at an additional mounting interface of the support arm. A pre-definable arrangement—of two rotation axes, for example—may in this way be provided with only three components, which can be mounted reversibly on one another.

According to one exemplary embodiment, the support system comprises at least two bushings which are mounted or can be mounted at a respective mounting interface at the support arm, wherein the mounting interfaces are respectively arranged at a free end of the support arm. The mounting interfaces are preferably of identical design. The respective mounting interface may in this way be formed by the same profile—in particular, by a continuous casting profile. With this embodiment, a boom/support arm may also be lengthened by an additional support arm. The mounting interfaces preferably respectively have receptacles for fastening means, which receptacles are arranged flush with the other mounting interface. The support arm may in this way be used expediently in the form of a profile, to which the forces may be applied on the same cross-section regions and transferred. For this, a symmetric force distribution and force transfer is preferable. According to one variant, the bushings respectively define a rotation axis. With two rotation axes provided at a respective end of the support arm by means of the bushings, these are preferably aligned at least approximately parallel to one another. Given this arrangement, a symmetrical introduction and transmission of force may be ensured. The support system can in this way stabilize itself.

According to one exemplary embodiment, a support system for a stand apparatus for arrangement in an operating theater comprises at least one bushing with a coupling part, by means of which the bushing can be mounted around a rotation axis at a spindle of the stand apparatus, and with a mounting segment by means of which the bushing can be reversibly mounted at a support arm of the stand apparatus, and also comprises the support arm or at least one additional support arm having a corresponding mounting interface, wherein the mounting segment and the mounting interface are set up to fasten the bushing and the support arm to one another in a positive and/or non-positive fit, without material bonding, in a predefined relative position so as to be reversibly assembled/disassembled, wherein the mounting segment has at least one lead-through for arrangement of a fastening means, wherein the mounting segment has at least one placement surface facing towards the rotation axis, on which placement surface a fastening means for transfer of a normal force acting radially outwardly in a radial direction essentially orthogonal to the rotation axis can be placed, wherein the mounting segment has a radially outwardly directed face which is designed to geometrically correspond to a face of the support arm, and wherein the bushing has a safety device to hold the support arm. The mounting segment has, in particular, a flat face surface which forms an interface with a geometrically correspondingly designed face surface of the mounting interface. A variety of the aforementioned advantages may in this way be realized in connection with one another.

The aforementioned object is also achieved via a stand apparatus for arrangement in an operating theater and for positioning/holding a medical technology device in said operating theater, comprising at least one bushing according to the disclosure and at least one support arm according to the disclosure, or comprising a support system according to the disclosure, wherein the stand apparatus has a connection module in the form of a spindle on which the support arm is or can be reversibly mounted by means of the bushing.

The present disclosure also concerns the use of a stand apparatus in an operating theater to position/hold a medical technology device, comprising at least one bushing and at least one support arm, wherein the stand apparatus has a connection module (in particular, in the form of a spindle) at which the support arm is reversibly mounted by means of the bushing, wherein the bushing has a mounting segment, wherein the support arm has a mounting interface, and wherein the mounting segment and the mounting interface are designed to geometrically correspond to one another. The modular design may in this way be used to set or readjust the apparatus. In other words, the aforementioned object is also achieved via a use of a stand apparatus in the operating theater to position/hold a medical technology device, comprising at least one bushing and at least one support arm, wherein the bushing has a mounting segment by means of which the bushing is reversibly mounted at a mounting interface of the support arm.

BRIEF DESCRIPTION OF THE SEVERAL VIEWS OF THE DRAWINGS

In the following figures, the disclosure will be explained in greater detail with the help of an exemplary embodiment. These show.

DETAILED DESCRIPTION

In connection with the description of the following figures, the reference indicators, in the event that they are not explicitly explained in individual figures, refer to the additional figures.

Figure 1A:
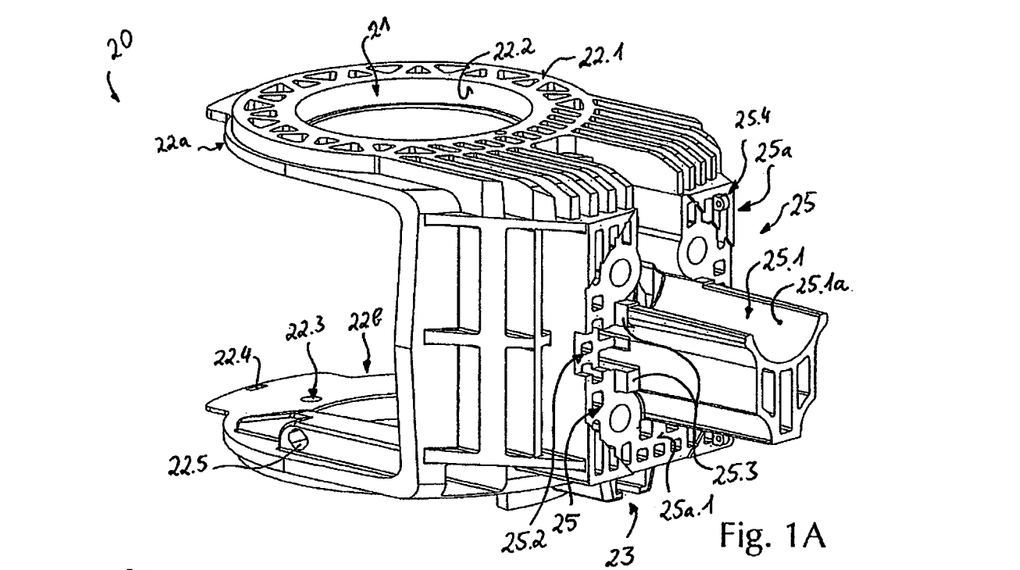
FIGS. 1A, 1B, 1C—respectively, in a perspectival view, a bushing according to an exemplary embodiment of the disclosure.
Figure 1B:
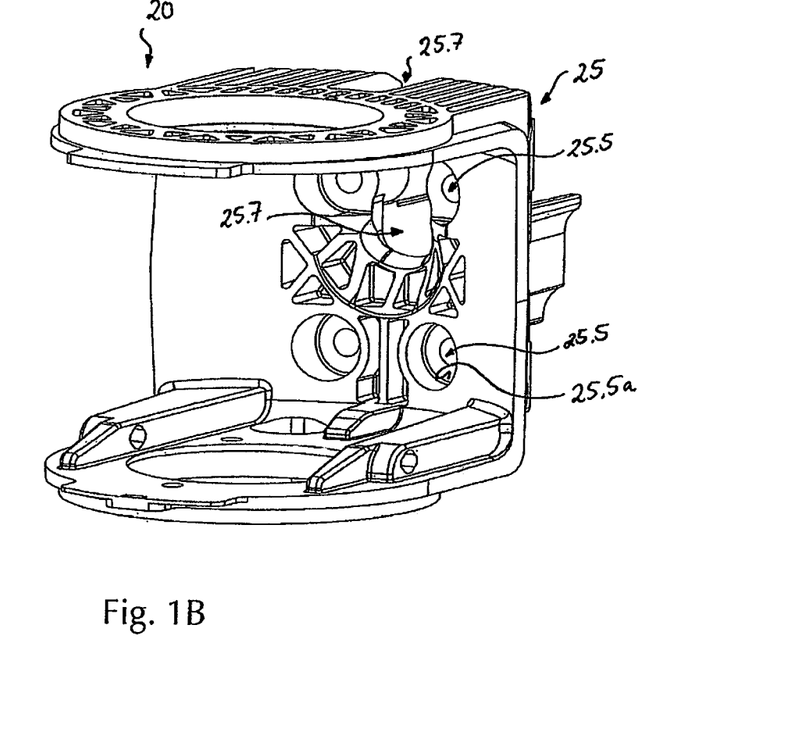
Figure 1C:
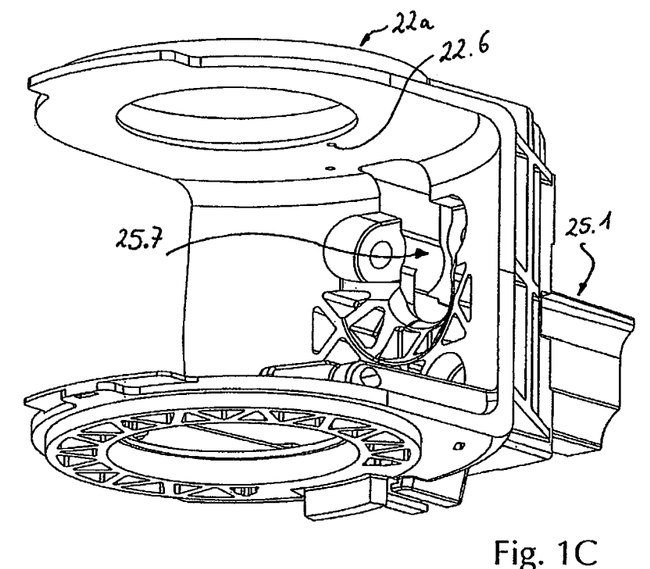

In FIGS. 1A, 1B, 1C, a bushing 20 is shown which is set up to be mounted so as to be rotatable on a spindle (not shown). The bushing has a coupling part 21 and a mounting segment 25, wherein the coupling part 21 is essentially formed by an upper annular segment 22a and a lower annular segment 22b. A support arm (not shown) may be fastened to the mounting segment 25.

Shown in FIG. 1A is the bushing 20 from the side of the mounting segment 25, wherein a face 25a is visible. The face 25a has a face surface 25a.1 that is flat, at least in sections. A support arm may be placed on the face surface 25a.1, and normal forces may be transmitted—in particular, to ensure [sic] a non-positive fit via static friction. Formed on the face 25a is a first positive-fitting safety segment 25.2 to counter vertical movement and/or twisting and a second positive-fitting safety segment 25.3 to counter axial movement and/or twisting. An eyelet bolt 25.4 is also indicated for screwing down a casing.

The first positive-fitting safety segment 25.2 is preferably a cutout or a recess or depression and has an upper and a lower surface. A pin 13.1c of the support arm 13 (see FIG. 3A) may be held in position between these two surfaces. One or more safety segments/cutouts, such as first positive-fitting safety segment 25.2, may jointly receive large torsion moments and secure the support arm against twisting—in particular, with large dynamic impulses or moments when the support arm strikes in a jerky manner on an upper or lower stop. A gap between the first positive-fitting safety segment 25.2 and the support arm is preferably small—approximately 0.1 mm.

The second positive-fitting safety segment 25.3 preferably does not rest so closely on the support arm. It also thereby transfers barely any torsion moments, or none at all. The second positive-fitting safety segment is set up to position the boom horizontally—in particular, in order to be able to assemble fastening elements/bolts in a simple way.

The mounting segment 25 has a safety device 25.1 for the support arm, at/on which the support arm may be supported. The safety device 25.1 is preferably designed as a longitudinal profile segment that projects radially from the bushing 20. The safety device 25.1 has a support segment, a support surface, and/or a support contour 25.1a on which a corresponding segment of the support arm can be borne. To mount the support arm 13 at the bushing 20, the safety device 25.1 can thus be inserted into an axially extending interior 13.6 of the support arm 13 (see FIGS. 1A, 3A, and 5). The support contour 25.1a thereby comes to be placed on a corresponding bearing surface 13.4c at the bearing segment 13.4b of the support arm 13 (see FIGS. 3A and 3B).

The upper annular segment 22a of the coupling part 21 has a face surface 22.1 at which an additional component (for example, an additional bushing) may be arranged. Each annular segment has an inwardly facing shell surface (bearing seat) 22.2 on which the bushing 22 can be mounted around the spindle.

The lower annular segment 22b of the coupling part 21 has multiple recesses 22.3 for locking a slip ring, as well as multiple reliefs 22.4—in particular, through-holes—for locking a cover cap. One or more threaded holes 22.5 for braking screws are also provided.

A receptacle 23 for a locking bolt for setting a stop position or rotation position is also provided on the underside of the bushing 20.

In FIG. 1B, the bushing 20 is shown from an inner side, from which fastening means (not shown) can be mounted. The mounting segment 25 has four lead-throughs 25.5 for fastening means—in particular, for bolts. A placement surface 25.5a for fastening means is formed at each lead-through 25.5. The mounting segment 25 also has a recess 25.7 for conduits or cables, which is arranged between two lead-throughs 25.5 for fastening means. The support arm 13 is thus to be affixed on the bushing 20 (see FIG. 5) via at least one (preferably four) fastening means 40 that flank the safety device 25.1 at one or more corners (in particular, four corners), so that a connection between the support arm 13 and the bushing 20 is achieved that is both rotationally fixed and tight in the axial direction (thus, along the longitudinal axis L) of the support arm 13 or, respectively, in the radial direction of the bushing 20.

In FIG. 1C, it is apparent that the safety device 25.1 forms the lower segment of the recess 25.7. Provided on an underside of the upper annular segment 22a are threaded holes 22.6 for the fastening of cable guidance means.

Figure 2A:
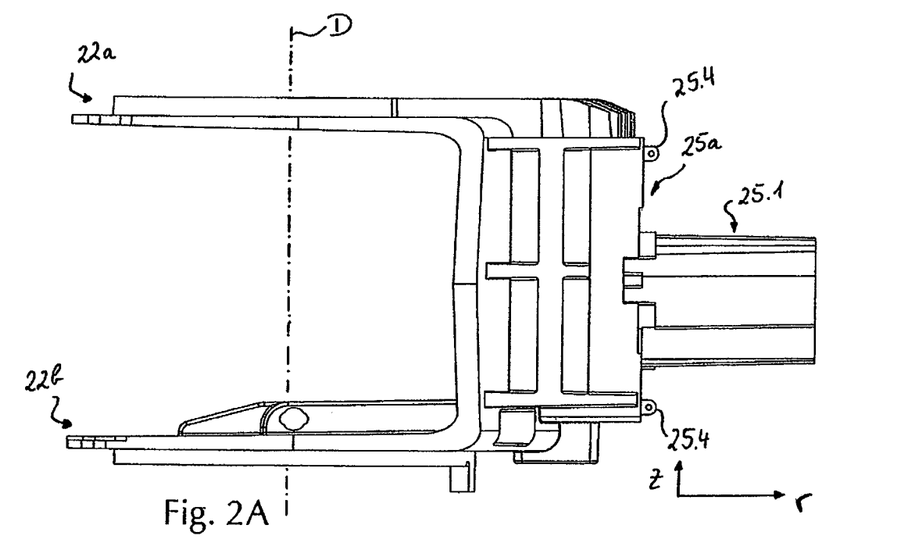
FIGS. 2A, 2B, 2C—respectively in a side view, or in a plan view from above or below, the bushing shown in FIGS. 1A, 1B, 1C.
Figure 2B:
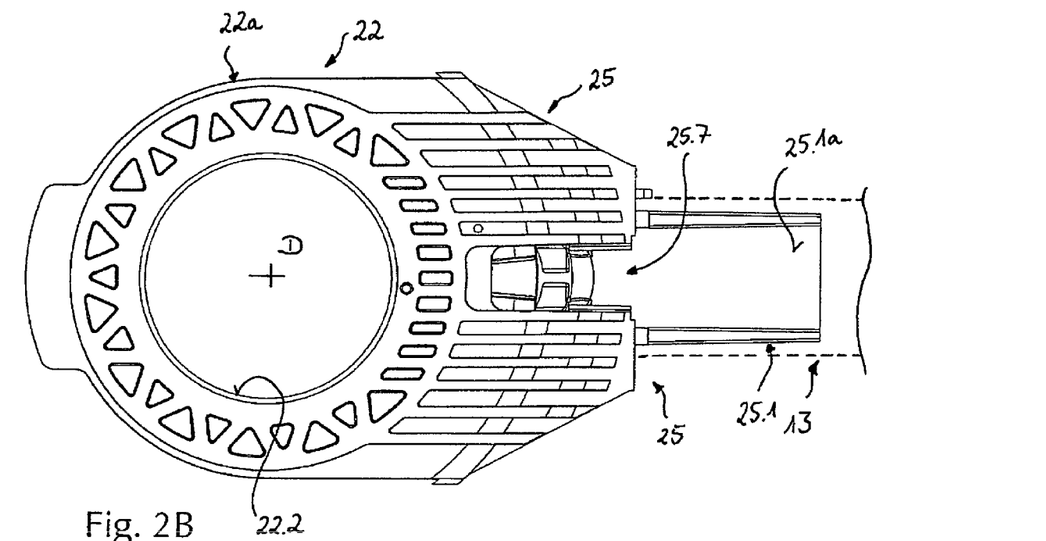
Figure 2C:
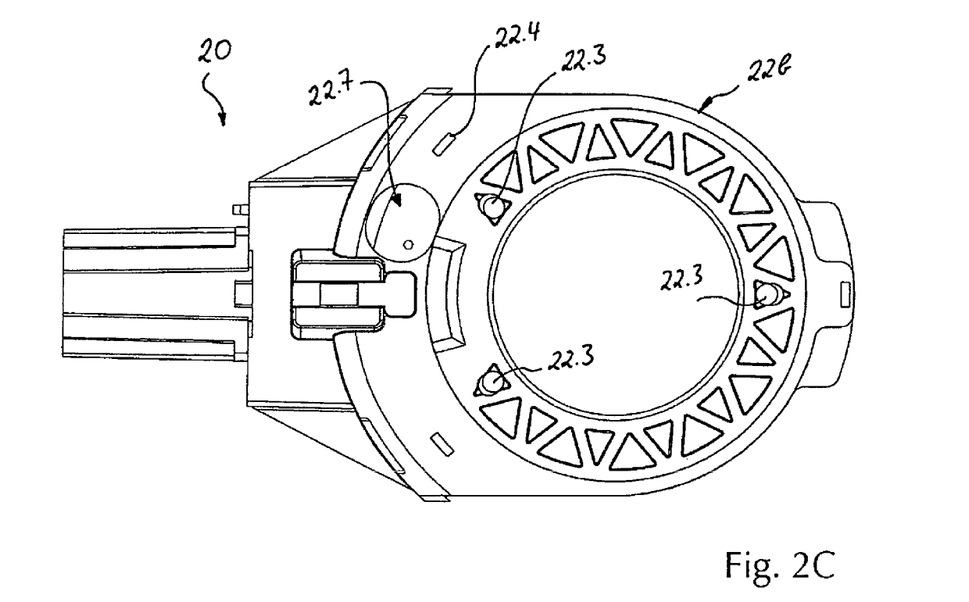

The design of the bushing 20 is shown in additional views in FIGS. 2A, 2B, 2C.

In FIG. 2A, the bushing 20 is shown in an alignment in which the radial direction r corresponds to the horizontal direction. In this alignment, the bushing 20 is preferably mounted so that the bushing 20 may rotate around a vertically aligned rotation axis. The rotation axis D defined by the annular segments 22a, 22b is aligned exactly in the vertical direction z. The face 25a extends in a plane orthogonal to the radial direction r. The safety device 25.1 extends in the radial direction r.

In FIG. 2B it is apparent that the recess 25.7 is formed only in the mounting segment 25, but not in the annular segments 22a, 22b. Cables or conduits may be guided from the support arm (not shown) through the recess 25.7 between the upper annular segment 22a and the lower annular segment in the direction of the rotation axis D.

In FIG. 2C, it is apparent that the support segment, the support surface, or the support contour 25.1a of the safety device 25.1 are formed by a self-contained surface which is as large as possible with regard to the width of the support arm 13 indicated by the dashed line. The width of the support segment 25.1a is, in particular, at least half, and preferably at least ⅗, of the width of the support arm. Greater loads may in this way be transferred without stress peaks, or without the risk of deformation of the profile of the support arm. One or more recesses 22.7 for conduits or cables are provided on an underside of the lower annular segment 22b. In other words, cables may optionally be directed between the annular segments at the spindle (not shown), or downward or upward out of the bushing 20. The cable guidance is an aspect which must be considered with support systems of modular design, since, in most instances, the medical technology devices held by the support system require a plurality of electrical or other supply lines. The bushing 20 enables different arrangement variants for these conduits, and thereby remains mountable in a simple manner.

Figure 3A:
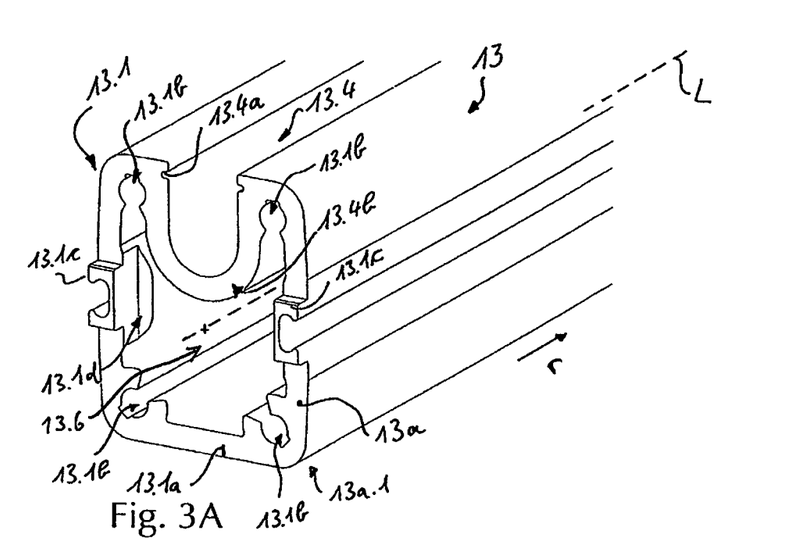
FIGS. 3A, 3B, 3C, 3D—respectively in perspectival view or in a frontal view, a support arm for a bushing or a stand apparatus according to an exemplary embodiment of the disclosure.
Figure 3B:
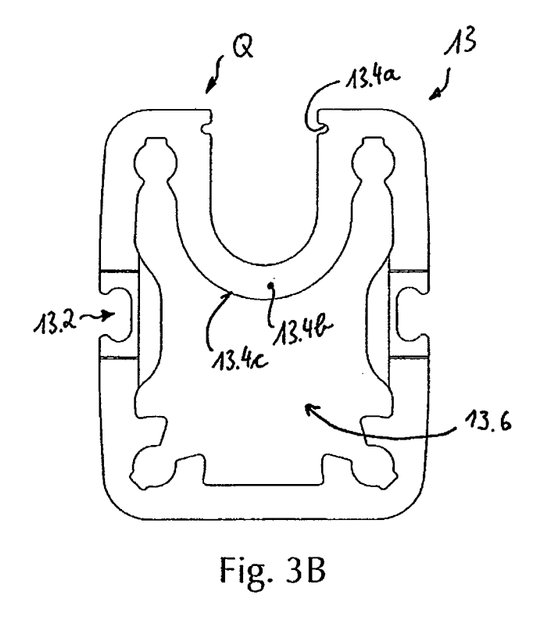
Figure 3C:
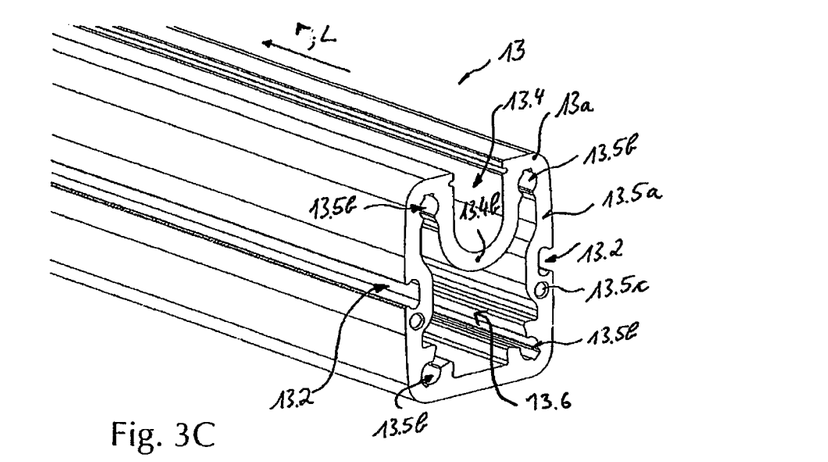

Shown in FIGS. 3A, 3B, 3C is the cross-section profile Q of a support arm 13 extending along a longitudinal axis L. In a state in which it is mounted on the previously described bushing 20, the longitudinal axis L is aligned in the radial direction r. The support arm 13 is formed by a circumferential wall 13a which satisfies at least three functions—in particular, a fastening, a securing, and/or a centering, as well as an arrangement of cables.

In FIG. 3A, a first mounting interface 13.1 is shown, wherein the mounting interface 13.1 is formed essentially by a face or face surface 13.1a of the support arm 13. Formed at the mounting interface 13.1 are four receptacles 13.1b—in particular, in the form of screw channels for fastening means. The receptacles 13.1b are thereby formed in the wall 13a.

Formed at the mounting interface 13.1 are pins 13.1c for rotation locking and vertical positioning, as well as cutouts 13.1d for horizontal positioning.

The wall 13a has four corners or folds 13a.1 in which the receptacles 13.1b are arranged.

The wall 13a also forms a channel 13.4—in particular, a cable channel open at the top. Two grooves 13.4a for locking cable securing means are formed in an upper segment of the channel 13.4.

The wall 13a has a bearing segment 13.4b which is set up to be borne at/on the geometrically corresponding safety device 25.1.

Visible in FIG. 3B is a bearing surface 13.4c formed on the bearing segment 13.4b, on which bearing surface 13.4c can be borne the support arm 13 on the safety device 25.1. The bearing surface 13.4c and the support surface 25.1a of the safety device 25.1 preferably have at least approximately the same curvature radius. FIG. 3B shows that the bearing segment 13.4b forms a U-profile. A large weight may in this way be accommodated. The U-profile can ensure a large carrying force and high dimensional stability. Thanks to the U-profile, the safety device 25.1 may be formed to be comparatively short in the radial direction. A groove 13.2 for fastening casing parts is provided on an outside of the wall 13a.

A second mounting interface 13.5 of the support arm 13 is shown in FIG. 3C. The mounting interfaces 13.1, 13.5 are respectively provided at a free end of the support arm 13—specifically, at the respective faces 13.1a, 13.5a. The mounting interface 13.5 comprises four receptacles 13.5b for fastening means—in particular, in the form of screw channels. The receptacles at both mounting interfaces are preferably of identical design. Also provided on the face 13.5a are pin holes 13.5c extending in the radial direction r or, respectively, in the longitudinal direction L, for rotation locking and for vertical positioning. Pins for alignment and securing of an additional bushing (cf. FIGS. 4A, 4B) may be introduced into these pin holes 13.5c.

Figure 3D:
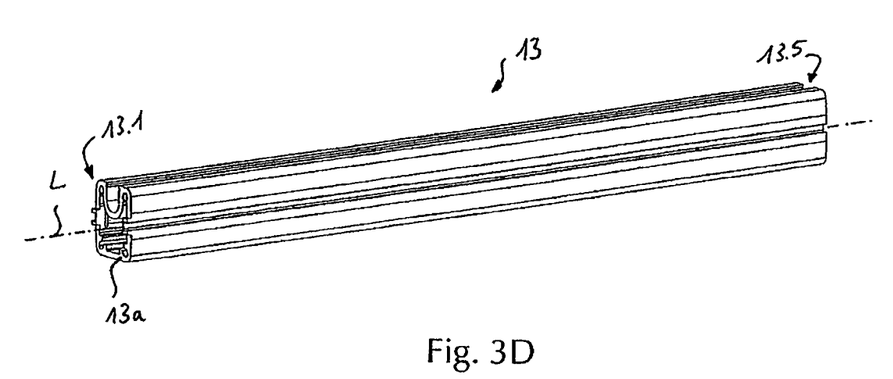

The support arm 13 is shown in its entirety in FIG. 3D. The mounting interfaces 13.1, 13.5 are respectively provided at a free end of the support arm 13. It is apparent that the support arm 13 is shaped in the form of an extruded profile extending in a straight line along the longitudinal axis L.

Figure 4A:
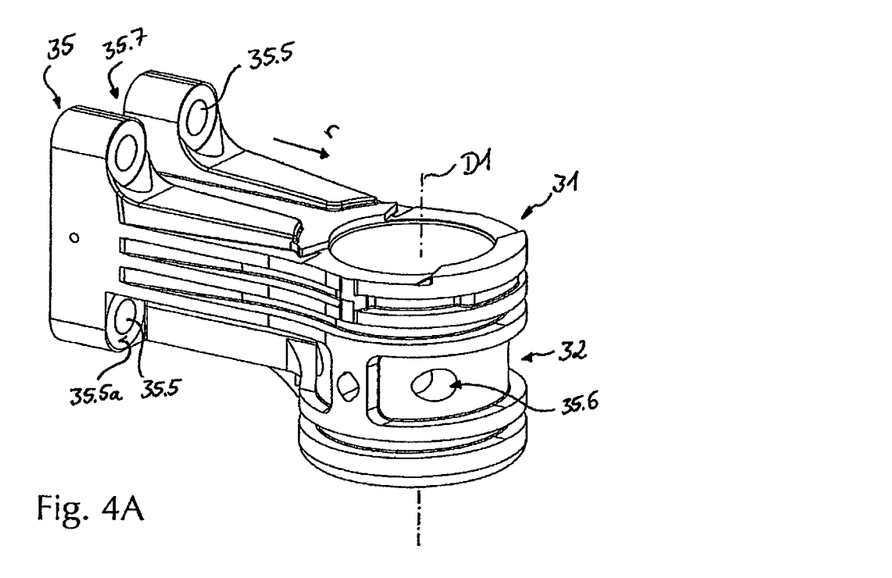
FIGS. 4A, 4B—respectively, in a perspectival view, an additional bushing according to an exemplary embodiment of the disclosure.
Figure 4B:
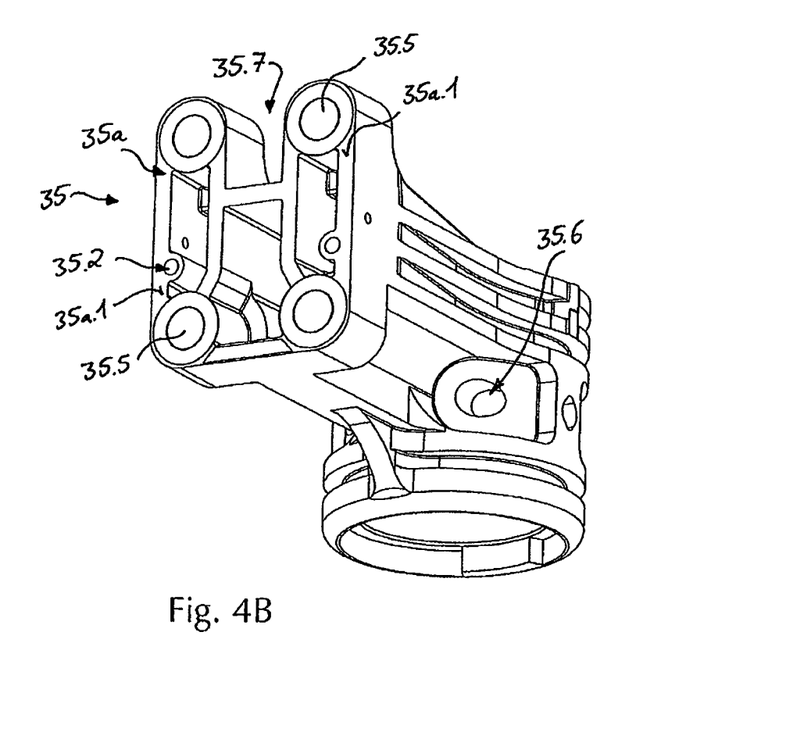

Shown in FIGS. 4A, 4B is an additional bushing 30 which defines an additional rotation axis D1. The additional bushing 30 is preferably mounted on a forward end of the support arm that faces toward a medical technology device. Like bushing 20, which may be a rear or first bushing, the additional bushing 30 has a coupling part 31 with annular segment 32, as well as a mounting segment 35. The mounting segment 35 has a face 35a having one or more face surfaces 35a.1, as well as four lead-throughs 35.5 for fastening means, wherein the lead-throughs respectively have a placement surface 35.5a for placement of the fastening means—for example, for placement of a screw head. The mounting segment 35 also has a positive-fitting safety segment 35.2 to counter vertical movement and/or twisting—here, in the form of two pin holes.

Via holes 35.6 that are flush with two of the lead-throughs are introduced at the coupling part 31. The via holes 35.6 facilitate the assembly radially from the outside. A recess 35.7 for conduits or cables is provided between two of the via holes 35.6, viz., the upper via holes 35.6.

Figure 5:
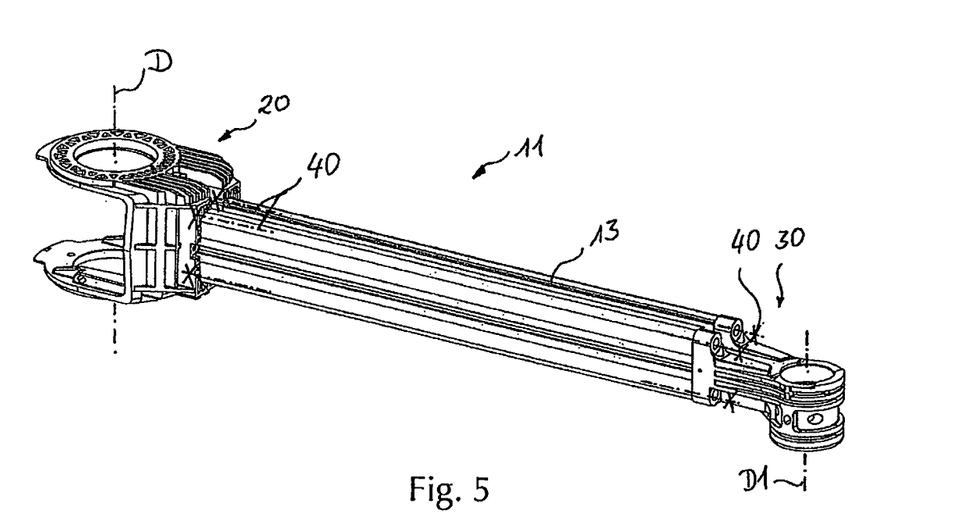
FIG. 5—in perspectival view, a support system or a portion of a support system—in particular, a boom with three components—according to an exemplary embodiment of the disclosure.

Shown in FIG. 5 is a boom 11 that can be mounted so as to rotate, comprising the bushing 20, which may be a rear bushing, and the additional bushing 30, which may be a forward bushing, as well as the support arm 13. Also indicated are fastening means 40 in the form of bolts.

Figure 6:
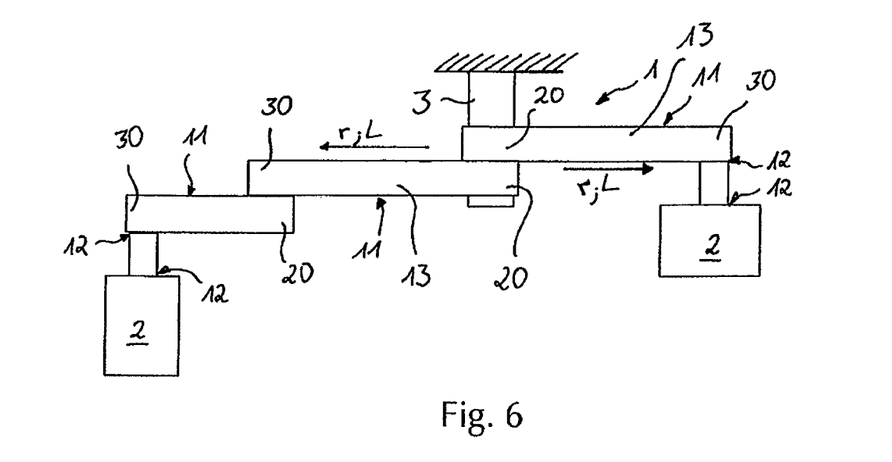
FIG. 6—in schematic depiction, a stand apparatus comprising a plurality of bushings and support arms according to an exemplary embodiment of the disclosure.

Shown in FIG. 6 is a stand apparatus 1 installed on a ceiling, which stand apparatus 1 comprises three booms 11 that respectively comprise the bushing 20, which may be a rear or first bushing, a support arm 13, and the additional bushing 30, which may be a forward bushing. Two of the support arms 13 are mounted so as to be rotatable on a spindle 3. The stand apparatus 1 positions and holds two medical technology devices 2 which are mounted in pivot joints 12 at the respective support arm 13 or the respective forward bushing 30.

LIST OF REFERENCE SYMBOLS 1 stand apparatus—in particular, ceiling stand apparatus
2 medical technology device—in particular, supply console
3 connection module—in particular, spindle
11 rotationally mountable boom, comprising two bushings and a support arm
12 pivot joint
13 support arm (spring arm)
13a circumferential wall
13a.1 corner or fold
13.1 first mounting interface—in particular, first face of the support arm
13.1a first face surface of the support arm
13.1b receptacle—in particular, screw channel for fastening means
13.1c pin for rotation locking and for vertical positioning
13.1d cutout for horizontal positioning
13.2 groove for fastening of casing parts
13.4 channel—in particular, cable channel open at the top
13.4a groove for locking cable securing means
13.4b bearing segment
13.4c bearing surface at the bearing segment
13.5 second mounting interface—in particular, second face of the support arm
13.5a second face surface of the support arm
13.5b receptacle for fastening means at the second mounting interface
13.5c pin holes for rotation locking and for vertical positioning
13.6 interior of the support arm
20 (first, rear) bushing set up for coupling to the connection module
21 coupling part
22a upper annular segment
22b lower annular segment
22.1 face surface
22.2 inwardly facing shell surface (bearing seat)
22.3 recess for locking a slip ring
22.4 relief—in particular, through-hole for locking a cover cap
22.5 threaded hole for braking screw
22.6 threaded hole for fastening of means for cable guidance
22.7 recess for conduits or cables
23 receptacle for bolts for adjustment of a stop position or rotation position
25 mounting segment
25a face
25a.1 face surface
25.1 safety device for support arm
25.1a support segment, support surface, or support contour 25.2 first positive-fitting safety device segment to counter vertical movement and/or twisting
25.3 second positive-fitting safety device segment to counter axial movement and/or twisting
25.4 screw eye for screwing down a casing
25.5 lead-through for fastening means—in particular, for screw
25.5a placement surface for fastening means
25.7 recess for conduits or cables
30 additional (forward) bushing arranged at the free end of the support arm
31 coupling part
32 ring segment
35 mounting segment
35a face
35a.1 face surface
35.2 positive-fitting safety device segment to counter vertical movement and/or twisting
35.5 lead-through for fastening means—in particular, for screw
35.5a placement surface for fastening means
35.6 via hole flush with the lead-through
35.7 recess for conduits or cables
40 fastening means—in particular, self-tapping screw
D rotation axis—in particular, vertically aligned normal axis
D1 rotation axis defined by the additional bushing
L longitudinal axis of the support arm
Q cross section profile of the support arm
r radial direction
z vertical direction The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A device for a stand apparatus for arrangement in an operating theater, comprising:
a bushing having a bottom surface, the bushing including:
a coupling part configured to be rotatably coupled to a spindle of the stand apparatus, the coupling part including an upper annular segment and a lower annular segment in spaced relationship and a rotation axis centrally disposed with respect to the upper and lower annular segments, the lower annular segment including a first surface and a second surface;
a threaded hole in the lower annular segment structured to receive a braking screw;
a recess in the first surface of the lower annular segment structured to lock a slip ring;
a mounting segment integral with the coupling part and configured to be coupled to a support arm of the stand apparatus; and
a receptacle extending from the bottom surface of the bushing structured to receive a locking bolt.

2. The device according to claim 1, wherein the mounting segment is configured to removably fasten the bushing to the support arm without material bond.

3. The device according to claim 1, wherein the mounting segment has at least one lead-through for receiving a fastener.

4. The device according to claim 3, wherein the at least one lead-through of the mounting segment has at least one placement surface configured to contact a head of the fastener when the fastener is received in the at least one lead-through.

5. The device according to claim 1, wherein the bushing comprises one of aluminum or an aluminum alloy.

6. The device of claim 1 wherein the threaded hole in the lower annular segment is one of a plurality of threaded holes in the lower annular segment, each threaded hole of the plurality of threaded holes structured to receive a respective braking screw.

7. The device of claim 1 wherein the recess is one of a plurality of recesses in the first surface of the lower annular segment, each recess of the plurality of recesses structured to lock the slip ring.

8. The device of claim 1 wherein the recess extends through the lower annular segment from the first surface to the second surface.

9. A system for an operating theater, comprising:
a first bushing having a bottom surface, the bushing including:
an upper annular segment;
a lower annular segment having a first surface and a second surface;
a first recess in the first surface of the lower annular segment configured to lock a slip ring; and
a receptacle extending from the bottom surface of the first bushing and structured to receive a locking bolt;
a support arm having at least one mounting interface configured to be removably coupled to the bushing; and
a second bushing removably coupled to the support arm opposite the first bushing,
wherein the at least one mounting interface of the support arm includes a first mounting interface and a second mounting interface, the first and second bushings mounted to the first and second mounting interfaces of the support arm, respectively,
wherein the first and second mounting interfaces are arranged at respective free ends of the support arm, and
wherein the first and second mounting interfaces are identical, and each include receptacles for receiving fasteners, which receptacles are flush with respective lead-throughs of the first and second bushings.

10. The system according to claim 9, further comprising a pin extending from the first mounting interface of the support arm, the pin received by a corresponding second recess in the first bushing.

11. The device of claim 9 further comprising:
a threaded hole in the lower annular segment of the first bushing structured to receive a braking screw.

12. The system of claim 9 wherein the first recess extends through the lower annular segment of the first bushing from the first surface to the second surface.

13. The system of claim 9 wherein the bottom surface of the first bushing includes the second surface of the lower annular segment.

14. The system of claim 9 wherein the first bushing further includes a threaded hole in a side of the lower annular segment structured to receive a braking screw.

15. A stand apparatus, comprising:
- at least one bushing having a coupling part including a first annular segment spaced from a second annular segment, the coupling part coupled to a spindle of the stand apparatus, the at least one bushing rotatable about a rotation axis centrally disposed with respect to the coupling part, the second annular segment including a first surface and a second surface opposite the first surface, the at least one bushing further including a threaded hole in a side of the second annular segment structured to receive a braking screw and a recess in the first surface of the second annular segment structured to engage a slip ring; and
- a support arm removably coupled to the at least one bushing, the support arm having a first mounting interface with at least one receptacle extending therethrough, the at least one receptacle aligning flush with a corresponding at least one lead through of the at least one bushing, wherein the at least one receptacle and the at least one lead through receive a fastener for removably coupling the support arm to the at least one bushing at the first mounting interface.

16. The stand apparatus of claim 15 wherein the support arm includes a pair of opposing pins extending from sidewalls of the support arm, each of the pair of opposing pins received in corresponding ones of a pair of opposing recesses in the at least one bushing.

17. The stand apparatus of claim 15 further comprising a second bushing, the support arm having a second mounting interface and the second bushing including a face mating with the second mounting interface when the second bushing is coupled to the support arm, the face of the second bushing further comprising a first pair of opposing pin holes and the second mounting interface further comprising a second pair of opposing pin holes, wherein pins for aligning and securing the second bushing to the support arm are received in corresponding ones of the first and second pairs of opposing pin holes.

18. The stand apparatus of claim 15 wherein the at least one bushing has a bottom surface, the stand apparatus further comprising:
- a receptacle extending from the bottom surface of the at least one bushing and structured to receive a locking bolt.

* * * * *